(12) United States Patent
Fahey et al.

(10) Patent No.: US 10,052,479 B2
(45) Date of Patent: Aug. 21, 2018

(54) SYSTEMS AND METHODS TO REDUCE SENSOR INTERFERENCE ASSOCIATED WITH ELECTRICAL THERAPIES

(71) Applicant: SAGE PRODUCTS, LLC, Cary, IL (US)

(72) Inventors: Brian J. Fahey, Palo Alto, CA (US); Timothy Machold, Moss Beach, CA (US); Zachary J. Malchano, San Francisco, CA (US); Curtis Tom, San Mateo, CA (US)

(73) Assignee: Sage Products, LLC, Cary, IL (US)

( * ) Notice: Subject to any disclaimer, the term of this patent is extended or adjusted under 35 U.S.C. 154(b) by 0 days.

(21) Appl. No.: 14/769,511

(22) PCT Filed: Mar. 12, 2014

(86) PCT No.: PCT/US2014/024435
§ 371 (c)(1),
(2) Date: Aug. 21, 2015

(87) PCT Pub. No.: WO2014/150872
PCT Pub. Date: Sep. 25, 2014

(65) Prior Publication Data
US 2016/0001070 A1    Jan. 7, 2016

Related U.S. Application Data

(60) Provisional application No. 61/801,002, filed on Mar. 15, 2013.

(51) Int. Cl.
*A61N 1/36* (2006.01)
*A61N 1/08* (2006.01)
(Continued)

(52) U.S. Cl.
CPC ...... *A61N 1/36003* (2013.01); *A61B 5/04012* (2013.01); *A61B 5/7217* (2013.01);
(Continued)

(58) Field of Classification Search
CPC .............. A61N 1/0492; A61N 1/36003; A61N 1/36014; A61N 1/36; A61N 1/08; A61B 5/00; A61B 5/04
(Continued)

(56) References Cited

U.S. PATENT DOCUMENTS 4,964,402 A    10/1990  Grim et al.
5,650,090 A    7/1997   Salyer
(Continued)

FOREIGN PATENT DOCUMENTS

| EP | 1100419 B1 | 5/2008 |
| WO | WO-96/18364 | 6/1996 |
| WO | WO-2012/003451 | 1/2012 |

OTHER PUBLICATIONS

Extended European Search Report for EP Application No. 14771130.3, dated Sep. 30, 2016, 6 pages.

*Primary Examiner* — Carl H Layno
*Assistant Examiner* — Jon Eric C Morales
(74) *Attorney, Agent, or Firm* — Foley & Lardner LLP

(57) ABSTRACT

Methods and systems for reducing interference in a therapeutic energy delivery system by delivering an electrical therapeutic signal to a patient to provide a therapeutic benefit to the patient, and delivering an electrical counter signal to the patient that destructively interferes with an electrical interference signal resulting from delivering the electrical therapeutic signal.

15 Claims, 6 Drawing Sheets

(51) Int. Cl.
  *A61N 1/04* (2006.01)
  *A61B 5/04* (2006.01)
  *A61B 5/00* (2006.01)

(52) U.S. Cl.
  CPC ......... *A61N 1/0452* (2013.01); *A61N 1/0456* (2013.01); *A61N 1/0476* (2013.01); *A61N 1/0492* (2013.01); *A61N 1/08* (2013.01); *A61N 1/36014* (2013.01)

(58) Field of Classification Search
  USPC ............................................ 607/48; 600/384
  See application file for complete search history.

(56) References Cited

U.S. PATENT DOCUMENTS

| | | |
|---|---|---|
| 6,233,945 B1 | 5/2001 | Kohout |
| 2004/0024438 A1 | 2/2004 | von Hoffmann et al. |
| 2004/0122495 A1 | 6/2004 | Peterman et al. |
| 2007/0178579 A1 | 8/2007 | Brown et al. |
| 2007/0225674 A1 | 9/2007 | Molnar et al. |
| 2009/0187232 A1 | 7/2009 | Salim |
| 2010/0081963 A1 | 4/2010 | Gilhuly |
| 2011/0152972 A1 | 6/2011 | Doerr et al. |
| 2012/0226330 A1 | 9/2012 | Kolen et al. |
| 2012/0277818 A1 | 11/2012 | Stancer et al. |
| 2013/0030277 A1* | 1/2013 | Fahey .................... A61B 90/39 600/384 |
| 2015/0272775 A1 | 10/2015 | Chehab et al. |

\* cited by examiner

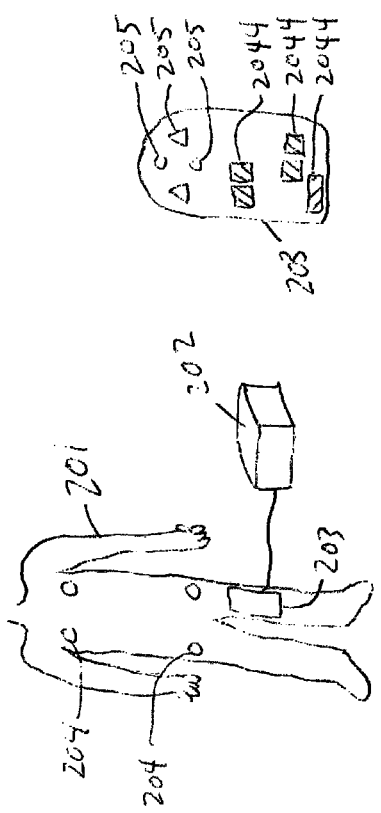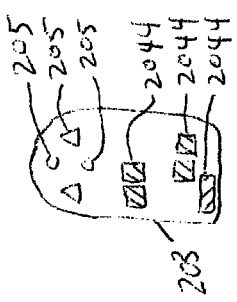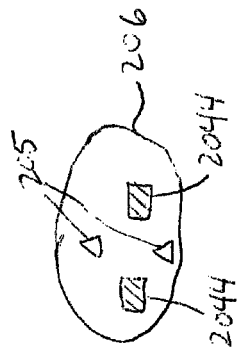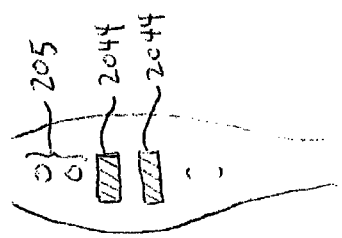

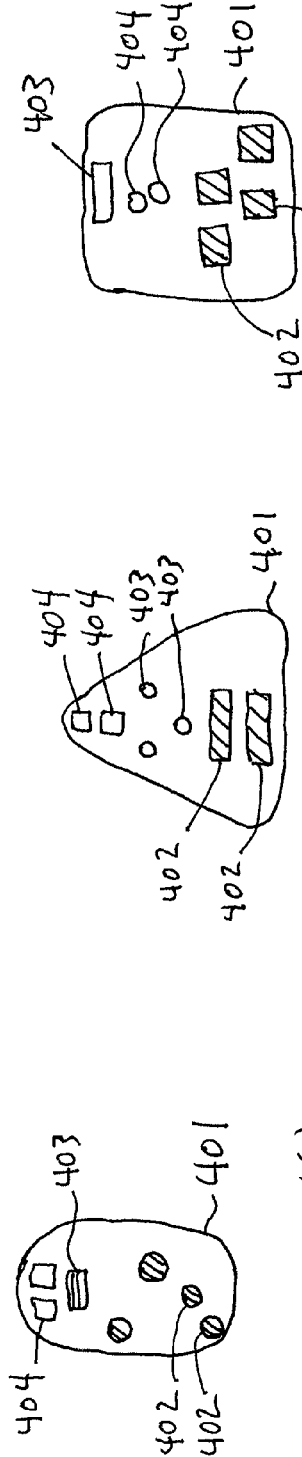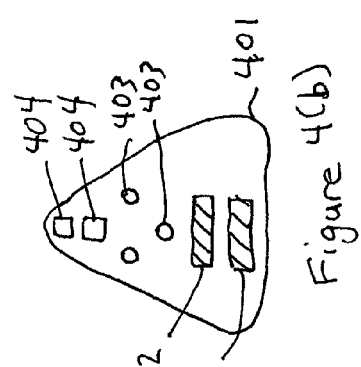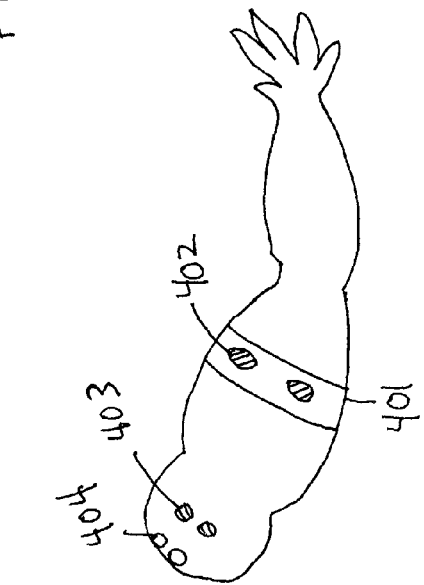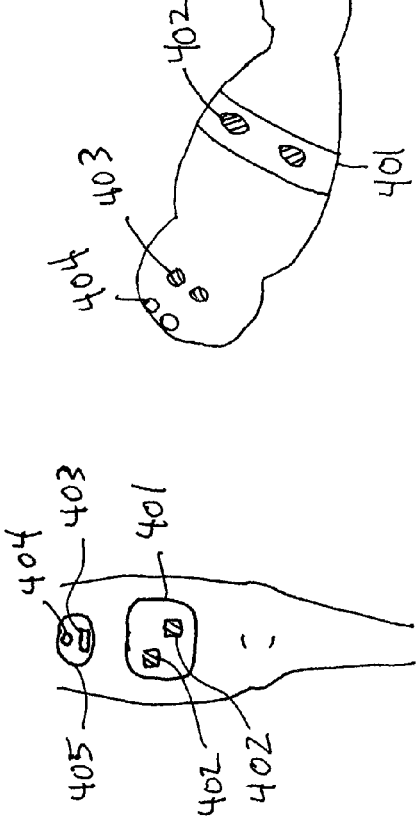

SYSTEMS AND METHODS TO REDUCE SENSOR INTERFERENCE ASSOCIATED WITH ELECTRICAL THERAPIES

CROSS REFERENCE TO RELATED APPLICATIONS

This application claims the priority of U.S. Prov. App. No. 61/801,002, filed Mar. 15, 2013, the disclosure of which is incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

BACKGROUND OF THE INVENTION

Neuromuscular electrical stimulation (NMES) (also referred to as powered muscle stimulation, functional muscle stimulation, electrical muscle stimulation, electrical stimulation, and other terms) is an established technology with many therapeutic uses, including pain relief, prevention or retardation of disuse atrophy, and improvement of local blood circulation. NMES is typically delivered as an intermittent and repeating series of short electrical pulses. In many implementations, these pulses are delivered transcutaneously by surface electrodes that are attached to a person's skin. Electrodes may be held to the skin through the use of straps, adhesives, or other mechanisms, and often contain a coupling layer composed of hydrogel that is capable of enhancing the efficiency of energy transfer from the electrode to the skin and underlying tissues.

A group of persons who could potentially show large benefit from NMES therapy are those who are being monitored medically for other conditions or as a standard part of their medical care. For example, many patients in the hospital are subjected to long periods of bed rest and develop atrophy that NMES could prevent. During hospitalization these patients are often connected to cardiac and other electrical monitors (ex. ECG) that measure/track certain aspects of the patient's health (for example, assessing potential arrhythmia and calculating heart rate). Similar statements may be made about subjects who might use NMES in other clinical settings or at home—electrical monitoring is often an important part of a patient's care that may drive either diagnostics or an intervention. Monitoring equipment may be external and temporary (ex. Holter monitor) or may be part of an implanted device that is permanent or semi-permanent. Monitoring and sensing capabilities may be stand-alone or integrated into another piece of medical equipment or device.

As NMES delivers electrical impulses to the body during its therapeutic application, there is the potential for interference with electrical monitoring equipment. For example, electrical signals delivered to the body as part of NMES treatment may be detected by sensors associated with other equipment, even in areas of the body remote to the site of NMES application. These NMES signals may alter or combine with (for example, through constructive or destructive interference) the physiological signals the sensors are intended to measure. If of sufficient amplitude, this interference may mask or alter signals detected by sensors in such a way that these signals are no longer reflective of the physiological event intended to be monitored. Accordingly, dangerous conditions may arise where a critical clinical event is not detected (for example, a cardiac arrhythmia goes undetected) or a device that implements sensing/monitoring behaves in an undesired fashion (for example, an implanted defibrillator shocks the patient during normal cardiac function because sensor interference is interpreted as a critical arrhythmia).

It is important to distinguish the situation currently described from the case of external electrical noise or other forms of external noise interfering with sensors. Sources of potential monitor interference arising from outside of the body are well-understood, and appropriate mechanisms are well-known in the art to prevent or limit substantial deleterious effects associated with these sources of noise. The presently-described situation, where sensor/monitor interference arises due to an electrical signal injected into or otherwise applied to the body, is much more challenging to handle and has limited available solutions.

The prior art illustrates some attempts to solve the interference problem described herein, but solutions described have inherent practical limitations. Solutions described in the prior art often use hardware or software-based signal filters that are applied to noisy data collected by sensors. Depending on the characteristics of both the desired and the interfering signals, these filters may be successful at removing the interference signal or minimizing its impact, allowing monitors and devices to function normally. Other solutions known in the art involve the use of additional sensors that are used in conjunction with the primary sensors associated with the monitor or device. These additional sensors may detect the interference signal, or a different combination of the desired and interference signals, and can be combined with data from the primary sensors in order to eliminate or minimize the impact of the interference signal on monitoring or sensing. For example, some systems described in the art use secondary sensors to measure the interference signal applied to the body, then subtract secondary sensor data from primary sensor data (which measures a combination of the desired physiological signal and the interference signal applied to the body) to minimize residual interference. Similar systems combine signals, sometimes from many additional sensors, in different ways (with or without the use of signal filters) to achieve similar goals.

The prior art systems noted above have practical limitations related to their implementation in the real-world. For example, to use filtering techniques to limit the impact of interference signals applied to the body, one would need access to sensor data following its detection but before it is interpreted, displayed, or otherwise used by algorithms/components later in a monitoring or device system's process. As a result, filters can be employed by the original manufacturers of monitoring equipment, but third-parties trying to prevent interference with existing equipment/monitors/sensors are prevented from implementing new filters as they generally do not have the proper access to make hardware or software modifications to existing equipment. Similar limitations are associated with a multiple-sensor approach; even in cases where the use of multiple sensors could help eliminate interference with measurements of physiological signals, these sensors cannot generally be added post-market to existing monitors or devices that measure and interpret data.

As one specific example, take the case of a patient in a hospital having his cardiac signals monitored with standard ECG equipment. ECG signals are measured by sensors (ECG electrodes) applied to the body and relayed to a processor/display unit via conventional leads that are well-known. If NMES is applied to the patient, signals detected by ECG electrodes may be a blend of the cardiac signals desired to be measured and an interference electrical signal produced as a byproduct of NMES treatment. Even if the NMES interference signal could be isolated and measured exactly with secondary sensors, there is no way to adjust the ECG electrode data with information from the secondary sensors without major modifications to the ECG monitoring system. In other words, the ECG sensor data is ported directly to the processer/display unit, and there is no practical way to intercept this data and adjust it using information from a secondary sensor before it is interpreted and displayed. Similar limitations are associated with the use of the filter approach. Thus, there is no way to prevent this type of signal interference using these methods without working directly with the ECG monitor manufacturer to implement them. As there are a vast possibility of devices and monitors that could suffer from interference from NMES devices and other devices that supply electrical signals to the body, collaborating with each manufacturer to implement to the techniques described in the prior art is impractical and thus these solutions aren't feasible for widespread use.

Novel solutions are needed to allow NMES and other devices to be used safely in the presence of monitoring and sensing equipment. These new approaches must solve the practical problems described above, and allow for interference reduction to be implemented in such a way that no modifications to monitoring devices are needed in order to reduce the interference produced by the therapy devices and subsequently detected by the sensors on the monitoring devices. Disclosed within are devices, systems, and methods for achieving these goals.

SUMMARY OF THE INVENTION

Detailed within are devices, systems, and methods for reducing the interference that electrically-based systems or therapies may produce in monitoring systems or devices that involve sensing electrical signals. Several embodiments and implementations of the invention are described herein, though it will be evident to those skilled in the art that these are exemplary and that numerous configurations of the present invention are possible. An important aspect of many of the embodiments of the present invention is that interference is reduced by preventing or limiting interference signals from reaching primary sensors associated with monitoring system or device sensors. As opposed to methods and systems described in the prior art, which use filters or secondary sensors to try to remove interference components from a combination signal (comprised of both desired and interference signal components) detected by primary sensors, the present invention seeks to prevent these interference components from reaching the primary sensor in the first place. Accordingly, no modifications of existing monitoring systems or devices is required in order to reduce or eliminate the impact of interference signals on the ability for these systems or devices to measure their target physiological signals. While much of this disclosure is written using the modality of NMES as an illustrative example, it will be obvious to those skilled in the art that with minor modifications the methods, devices, and systems described herein may be applied with utility to other energy-delivery therapies as well. Similarly, while interference with ECG monitoring will be used as an example, this should not be construed as limiting as the same inventions may be applied to minimize interference with other types of monitoring and/or devices. It should be appreciated that different aspects of the invention can be appreciated individually, collectively, or in combination with each other.

In a preferable embodiment, an NMES system is configured with multiple independent energy-delivery channels. One or more of these channels is used to apply NMES therapy to a body part. A by-product of this application of NMES energy is an interference signal that could inhibit the function of devices elsewhere on or in the body that monitor or sense electrical signals. To address this problem, other channels in the NMES system may be used to provide a counter signal which can interact and destructively interfere with the interference signal produced by the standard NMES waveforms. This counter signal has an amplitude and a phase such that, at monitoring locations remote to the site of NMES therapy, the interference signal produced by NMES energy delivery is eliminated or minimized. Some embodiments may have more energy channels dedicated to apply NMES to a body part than energy channels used to cancel the NMES interference signal remotely. This active cancellation approach is differentiated from the prior art because interference signals are addressed prior to them reaching the primary sensor associated with monitoring devices or other equipment—no alterations need to be made to existing equipment.

In preferable embodiments of the invention, the amplitude, phase, shape, and other properties of the counter signal may be adjusted by a user to achieve optimal results. In variation embodiments, the counter signal is fixed or adjusted automatically based on settings of the NMES device. In preferable embodiments, the electrodes used to deliver the counter signal to the body are located in a fixed location relative to the stimulation electrodes used to deliver NMES energy to the body. In variations of the preferable embodiments, the electrodes delivering the counter electrode signals may have adjustable locations relative to the region of NMES therapy.

In a variation of the preferable embodiment, sensors are integrated into the NMES system that measure the interference signals produced by the NMES treatment. In some embodiments, this measurement occurs remotely from the region being treated with NMES, while in some embodiments the sensing/measurement occurs locally. After sensors have measured the signal produced by NMES, internal systems are used to adjust and fine-tune the counter signals that are produced by the system in order to limit or eliminate interference with monitoring equipment or sensing devices.

In some embodiments, multiple independent energy delivery channels are used to produce the counter signal. In this embodiment, each independent energy channel may be configured to deliver energy to separate pairs or groups of electrodes, so that the counter signal may take on numerous shapes and properties. In other variations of a preferable embodiment, a single energy delivery channel interfacing with a single pair of skin-contact electrodes is used to provide to the counter signal to the body. In further variations, a monopolar configuration is implemented that uses a single electrode contact site to provide the desired counter signal.

An important aspect of preferable embodiments of the invention is that energy delivered to produce the counter signal does not interfere with or degrade the ability to successfully treat a patient or subject with NMES. In other words, the counter signal can effectively cancel the NMES interference signal at remote sensing locations but does not degrade the NMES electrical signal used to create muscle contraction in the region being treated with NMES. Any viable solution to the problems described herein must allow both the NMES system (or another energy-related therapy that is being applied) and the monitoring/sensing system to be used normally and effectively simultaneously.

The disclosed devices, methods, and systems are useful because they will enable effective NMES therapy in a subset of persons that currently may not qualify for it due to reliance on monitoring systems or devices. For example, the United States FDA currently requires device labeling for NMES systems indicating that they should not be used on patients with cardiac pacemakers or defibrillators, as there is a fear of the consequences of interference with the sensing systems in these devices. Novel devices, systems, and methods that could prevent interference with the sensing systems of cardiac devices would allow NMES therapy to reach a much larger group of patients who could benefit from the treatment. The presently-disclosed inventions will also allow NMES to be used more safely in hospital settings, particularly those settings which require patients to be connected to ECG or other monitoring systems continuously.

One aspect of the disclosure is a muscle stimulation system comprising a stimulation electrode configured to be secured to a patient to deliver an electrical muscle stimulation signal to the patient; and an counter signal electrode configured to be secured to the patient and relative to the stimulation electrode to deliver an electrical counter signal to the patient; and at least one controller adapted to generate the electrical muscle stimulation signal and the counter signal, wherein the electrical counter signal is adapted to destructively interfere with an electrical interference signal resulting from the electrical muscle stimulation signal.

In some embodiments the electrical counter signal is adapted such that it does not degrade the stimulating effect of the electrical muscle stimulation signal.

In some embodiments the electrical counter signal is adapted to minimize or eliminate the interference signal.

In some embodiments the electrical counter signal has an opposite polarity and substantially the same amplitude as the interference signal.

In some embodiments the electrical counter signal has an amplitude that is less than an amplitude of the electrical muscle stimulation signal.

In some embodiments the electrical counter signal has a shape that is different than a shape of the electrical muscle stimulation signal.

In some embodiments the at least one controller is adapted so that the electrical counter signal is fixed.

In some embodiments the at least one controller is adapted such that the electrical counter signal can be manually or automatically varied. The at least one controller can be adapted such that at least one of an amplitude, a phase, and a shape of the electrical counter signal can be manually or automatically varied. The at least one controller can be adapted to vary the electrical counter signal based on the electrical interference signal. The system can further include an interference signal sensor configured to be secured to the patient and to sense the electrical interference signal.

In some embodiments the system also includes an interference sensor configured to be secured to the patient and adapted to sense the interference signal at a location different than where the electrical muscle stimulation signal is delivered to the patient, wherein the electrical counter signal is based on the sensed interference signal.

In some embodiments the electrical counter signal is adapted to reduce interference between a sensed physiological signal from the patient and the interference signal. The physiological signal from the patient can be an EKG signal.

In some embodiments the system further comprises a pad configured to be positioned on the patient and comprises the stimulation electrode and the counter signal electrode. The pad can further comprise an interference sensor adapted to sense the electrical interference signal. The interference sensor can be disposed between the stimulation electrode and the counter electrode. The counter electrode can be disposed between the stimulation electrode and the interference sensor.

One aspect of the disclosure is a method of reducing interference in a muscle stimulation system comprising delivering an electrical muscle stimulation signal to a patient to stimulate muscle contraction; and delivering an electrical counter signal to the patient that destructively interferes with an interference signal resulting from delivering the electrical muscle stimulation signal.

In some embodiments delivering the electrical counter signal does not degrade the stimulating effect of the delivered electrical muscle stimulation signal.

In some embodiments delivering the electrical counter signal minimizes or eliminates the interference signal.

In some embodiments delivering the electrical counter signal comprises delivering an electrical counter signal that has an opposite polarity and substantially the same amplitude as the interference signal. Delivering the electrical counter signal can include delivering an electrical counter signal that has an amplitude less than an amplitude of the delivered electrical stimulation signal.

In some embodiments delivering the electrical counter signal comprises delivering an electrical counter signal that has a shape that is different than a shape of the electrical muscle stimulation signal.

In some embodiments the method further comprises modifying a parameter of the delivered electrical counter signal and delivering a second electrical counter signal with the modified parameter. Modifying a parameter of the delivered electrical counter signal can include modifying at least one of an amplitude, a phase, and a shape of the delivered electrical counter signal. Modifying a parameter of the delivered electrical counter signal can be in response to sensing the interference signal with an interference signal sensor.

In some embodiments the method further comprises sensing the interference signal with an interference signal sensor. Sensing the interference signal with an interference signal sensor can comprise sensing the interference signal at a location different than where the muscle stimulation signal is delivered to the patient and where the counter signal is delivered to the patient. Sensing the interference signal with an interference signal sensor can comprise sensing the interference signal at a location between where the muscle stimulation signal is delivered to the patient and where the counter signal is delivered to the patient.

In some embodiments delivering an electrical counter signal is in response to sensing the interference signal.

In some embodiments the method further comprises sensing a physiological signal from the patient, and wherein delivering the counter signal reduces interference between the sensed physiological signal and the interference signal. Sensing a physiological signal from the patient can comprise sensing an EKG signal from the patient, and delivering the counter signal can reduce interference between the EKG signal and the interference signal.

One aspect of the disclosure is a therapeutic energy delivery system comprising a therapeutic energy delivery element configured to be secured to a patient to deliver therapeutic energy to the patient; a counter energy delivery element configured to be secured to the patient and relative to the therapeutic energy element to deliver counter energy to the patient; and at least one controller adapted to generate the therapeutic energy and the counter energy, wherein the counter energy is adapted to destructively interfere with interference energy resulting from the therapeutic energy.

In some embodiments the counter energy is adapted such that it does not degrade the therapeutic effect of the therapeutic energy.

In some embodiments the counter energy is adapted to minimize or eliminate the interference energy.

In some embodiments the therapeutic energy is an electrical signal, the counter energy is an electrical signal, and the interference energy is an electrical signal. The counter signal can have an opposite polarity and substantially the same amplitude as the interference signal. The counter signal can have an amplitude that is less than an amplitude of the therapeutic signal. The counter signal can have a shape that is different than a shape of the therapeutic signal. The at least one controller can be adapted such that at least one of an amplitude, a phase, and a shape of the counter signal can be manually or automatically varied. The at least one controller can be adapted to vary the counter signal based on the interference signal.

In some embodiments the at least one controller is adapted such that the counter energy can be manually or automatically varied.

In some embodiments the system further comprises an interference sensor configured to be secured to the patient and adapted to sense the interference energy at a location different than where the therapeutic energy is delivered to the patient, wherein the counter energy is based on the sensed interference energy.

In some embodiments the counter energy is adapted to reduce interference between sensed physiological energy from the patient and the interference energy. The sensed physiological energy from the patient can be an EKG signal. The system can further include a sensor adapted to be secured to the patient at a location relative the therapeutic energy element and configured to sense the physiological energy from the patient.

One aspect of the disclosure is a method of reducing interference in a therapeutic energy delivery system comprising delivering an electrical therapeutic signal to a patient to provide a therapeutic benefit to the patient; and delivering an electrical counter signal to the patient that destructively interferes with an electrical interference signal resulting from delivering the electrical therapeutic signal.

In some embodiments delivering the electrical counter signal does not degrade the therapeutic effect of the delivered electrical therapeutic signal.

In some embodiments delivering the electrical counter signal minimizes or eliminates the interference signal.

In some embodiments delivering the electrical counter signal comprises delivering an electrical counter signal that has an opposite polarity and substantially the same amplitude as the interference signal. Delivering the electrical counter signal can comprise delivering an electrical counter signal that has an amplitude less than an amplitude of the delivered electrical therapeutic signal.

In some embodiments delivering the electrical counter signal comprises delivering an electrical counter signal that has a shape that is different than a shape of the electrical therapeutic signal.

In some embodiments the method further comprises modifying a parameter of the delivered electrical counter signal and delivering a second electrical counter signal with the modified parameter. Modifying a parameter of the delivered electrical counter signal can comprise modifying at least one of an amplitude, a phase, and a shape of the delivered electrical counter signal. Modifying a parameter of the delivered electrical counter signal can be in response to sensing the interference signal with an interference signal sensor.

In some embodiments the method further comprises sensing the interference signal with an interference signal sensor. Delivering an electrical counter signal can be in response to sensing the interference signal. Sensing the interference signal with an interference signal sensor can comprise sensing the interference signal at a location different than where the therapeutic signal is delivered to the patient and where the counter signal is delivered to the patient. Sensing the interference signal with an interference signal sensor can comprise sensing the interference signal at a location between where the therapeutic signal is delivered to the patient and where the counter signal is delivered to the patient.

In some embodiments the method further comprises sensing a physiological signal from the patient, and wherein delivering the counter signal reduces interference between the sensed physiological signal and the interference signal. Sensing a physiological signal from the patient can comprise sensing an EKG signal from the patient, and delivering the counter signal reduces interference between the EKG signal and the interference signal.

BRIEF SUMMARY OF THE DRAWINGS

As shown in FIG. 2, variations of preferable embodiments of the devices and systems that include electrodes used to deliver NMES and electrodes used to produce a counter signal.

As shown in FIG. 4, variations of preferable embodiments of the devices and systems that include electrodes used to deliver NMES and electrodes used to produce a counter signal as well as sensors used in conjunction with the system.

DETAILED DESCRIPTION OF THE INVENTION

The invention provides methods, devices, and systems for limiting the impact electrical-based therapies may have on monitoring systems and/or other devices that require sensing of electrical signals. Though this disclosure uses the modality of NMES as an illustrative example, those skilled in the art will appreciate that the presently-disclosed invention may be applied with utility to other energy-delivery therapies as well. Various aspects of the invention described herein may be applied to any of the particular applications set forth below or for any other types of electrical stimulation and sensing systems or methods. The invention may be applied as a standalone device, or as part of an integrated medical treatment system. It shall be understood that different aspects of the invention can be appreciated individually, collectively, or in combination with each other.

Figure 1A:
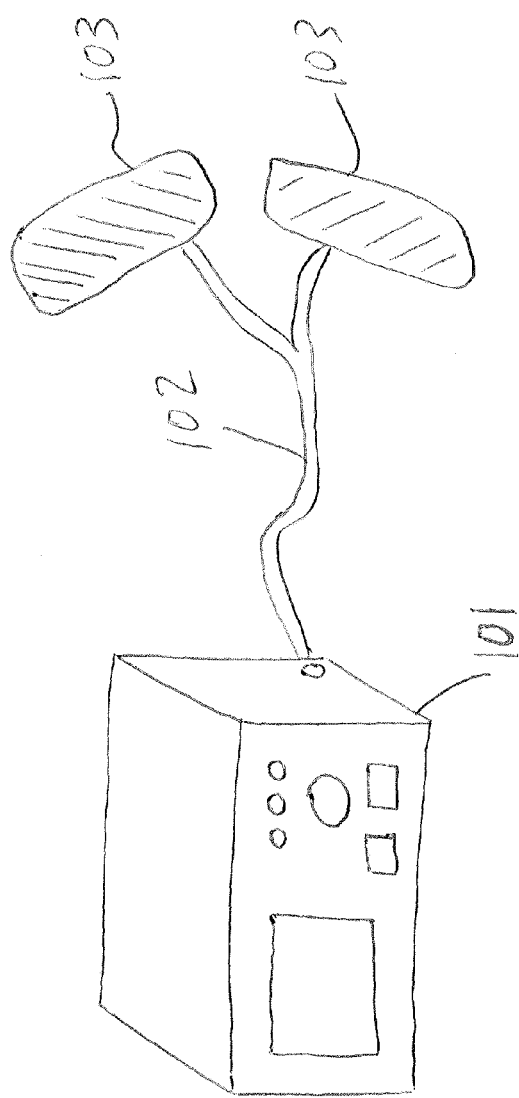
As shown in FIG. 1, an embodiment of the systems and devices described herein that demonstrates the main system components.

With reference to FIG. 1, in a preferable embodiment, the system includes three core components: surface electrodes that are used to couple electrical energy into and out of the body (104, 105), a stimulation control unit (101) that creates the stimulation energy and potentially other electrical pulses and delivers them to the surface electrodes, and a wired connection (102) to allow communication between the electrodes and control unit. In some variation embodiments, a wireless system using may be used that eliminates the need for a wired connection, instead using a radiofrequency transmission, optical, acoustic, or electromagnetic signals, or another suitable mechanism. In a preferable embodiment, the electrodes will be assembled into a custom pad (103) such that electrode layout and configuration will be pre-optimized for a particular region of the body. Some electrodes may be pre-designated to deliver stimulation energy that delivers NMES therapy (104), while others may be configured to produce counter signals (105) intended to prevent the NMES therapy from creating meaningful interference in remote sensors that are intended to measure electrophysiological signals. In some embodiments, electrodes may be used both to deliver NMES therapy and to deliver counter signals, and/or may be designated by the user or control unit to produce one type of signal or the other at the time of NMES treatment. The control unit is a separate unit that may be located some distance from the person receiving therapy. In an alternate embodiment, the control unit may be integrated into a housing unit containing the stimulating electrodes, or in another way be adapted to reside proximate to the region of NMES.

In a preferable embodiment, the control unit contains components such as a signal generator, memory, processor, and power supply. The primary operation of the control unit may be provided by a microprocessor, field programmable gate array (FPGA), application specific integrated circuit, some combination of these mechanisms, or other suitable mechanism. Electrical transformers or another suitable mechanism is used to produce electrical energy pulses that may be delivered to the body of a subject. When activated, the control unit generates electrical signals that are transmitted to the surface electrodes in the pad, which couple the energy into the body (for example, to activate muscles). Some electrical stimulation parameters, including the duration of therapy, are adjustable by the operator through buttons, knobs, dials, or switches on the control unit. Other electrical stimulation parameters, such as stimulation pulse energy amplitude, may be adjusted by the user through control unit controls or be automatically optimized using automatic algorithms implemented by the control unit. The control unit may also contain items such as a touchscreen or other form of display and/or user interface, data acquisition channels and associated hardware/software, and other safety-control features.

In a preferable embodiment, the control unit is capable of transmitting electrical pulses on at least one and preferably many more (ex. 6-12) channels simultaneously and independently. In some embodiments, the control unit may also be capable of creating arbitrary phase delays between pulses originating from different channels. In variations of these embodiments, the control unit may transmit pulses on some channels dependently and others on different channels independently.

Figure 1B:
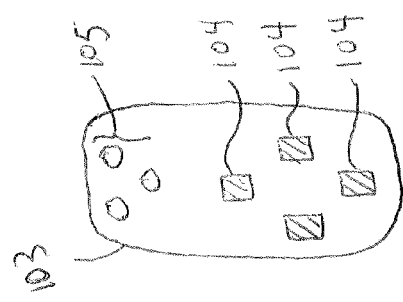

In a preferable embodiment, the system electrodes are arranged on a pad in an array with a predetermined layout (see, for example, FIG. 1(b)). In a preferable embodiment, the pads are comprised of a thin and flexible housing with an adhesive backing to facilitate maintenance of skin contact with the person receiving NMES. More than one adhesive material may be used; for example electrode contact areas may use a hydrogel or similar backing while other pad areas may be secured with a more gentle adhesive (ex. those used in bandages). The hydrogel backing for electrodes will also enhance the coupling of electrical energy and signals between stimulation electrodes and the person's body. The pad contains two or more strategically-placed surface electrodes that are used to deliver electrical energy to muscles and/or nerves in order to produce muscle contraction, as well as one or more electrodes used to produce a counter signal. In variation embodiments, electrodes may be discretely-placed in contact with tissue independent of a larger pad (as in FIG. 2(d)). In some embodiments, a system pad may also contain a small and lightweight control unit that is intended to sit proximate to the region of tissue being treated. In some embodiments, more than one pad may be used, with each pad containing at least one electrode that produces either a stimulating or counter signal.

In preferable embodiments the system will be configured specifically for a particular region of the body intended to receive NMES. Referring to FIG. 2, a system is shown configured for use with muscle stimulation of the left quadriceps. A control unit (202) is shown to connect to a pad containing electrodes (203) through a wired connection. Also shown are common locations for ECG electrodes (204) which are used to monitor the subject's cardiac activity. In preferable embodiments of the system, electrodes used to deliver the counter signal to the body will lie between the monitoring system sensors and the electrodes used to deliver NMES therapy. In the example shown, the counter-signal electrodes thus lie between the quadriceps and the torso. In FIG. 2(b), a detailed view of one embodiment of a system pad (203) is shown, with example locations of stimulation electrodes (2044) and electrodes used to deliver the counter signal (205). Note the counter signal electrodes would fall between the NMES electrodes and the ECG measuring electrodes of the monitoring system. A different implementation of this embodiment is shown in FIG. 2(c), where the counter signal electrodes are arranged differently relative to the stimulation electrodes, primarily because the pad (206) has been configured to deliver therapy to a different anatomical location (for example, the back). In FIG. 2(d), an embodiment of the system is shown where no pad is used; both types of electrodes are placed discretely on the skin at locations of the operator's choosing, and are not fixed in position relative to one another.

Figure 3A:
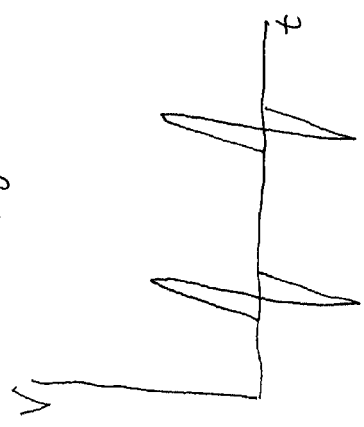
As shown in FIG. 3, various electrical signals associated with the devices, systems, and methods described herein.
Figure 3B:
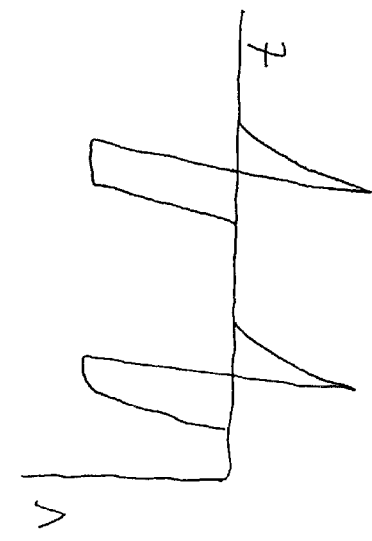

During the process of NMES, electrical energy is generally delivered between at least two electrodes in a set. The bulk of electrical energy travels between the electrodes in the set, though fields of energy spread away from the stimulation region. It is these fields which can create interference problems for monitoring in remote regions. An example is provided in FIG. 3. In (a), a sample signal produced by the control unit is shown (x-axis is time, y-axis is voltage, not to scale). This is one example of an asymmetric, biphasic square wave commonly used in NMES. In FIG. 3(b), an example signal that can be measured just outside the region of stimulation (in the area marked as (1) in FIG. 3(e)) is shown. The overall energy amplitude is lower (not to scale), and the shape is somewhat different than the original signal shown in (a). However, the pulse width and the polarity may be similar. In (c), an example signal measured in a location even more remote from the NMES site (region (2) of FIG. 3(e)) is shown. Though the same shape and pulse width as the signal shown in (b), this signal measured more remote from the region of stimulation has relatively lower amplitude.

Figure 3C:
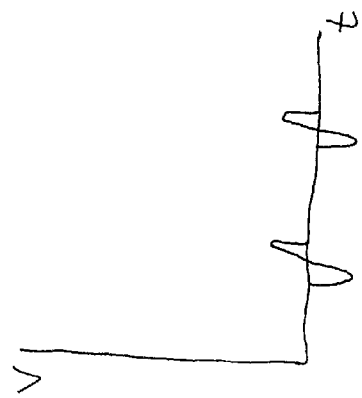
Figure 3D:
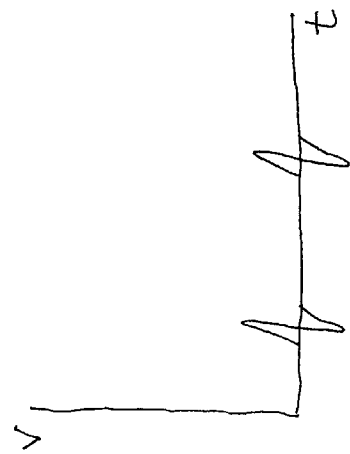
Figure 3E:
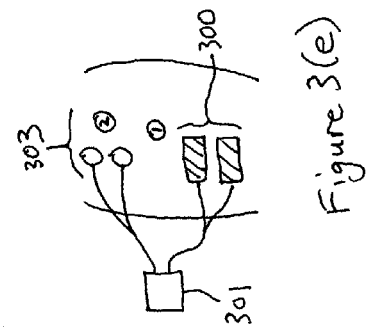

One embodiment of the presently-disclosed devices, systems and methods operates by producing the inverted version of the signal shown in FIG. 3(c) and delivering it to the body at an appropriate location (for example, near region (2) of FIG. 3(e)). We refer to this inverted signal as the counter signal, an example of which is shown in FIG. 3(d). By producing an opposite polarity but equal amplitude counter signal using counter signal electrodes (303), it is possible to cancel out the interference signal originating from the stimulation region (region of electrodes (302)) and prevent it from spreading into more distal regions. Counter signal characteristics may be matched so that the propagation characteristics of the counter signal are similar to those of the NMES interference signal, allowing for the impact of the interference signal to be minimized over considerable distances.

The amplitude of the counter signal is important to note. As described above, to be practical any counter signal needs to minimize the effect of the NMES interference signal on remote monitoring and/or sensing devices, but also not meaningfully impact the effectiveness of the NMES itself. Since in general counter signals are required to be of relatively small amplitude (especially relative to stimulation signals, for example that shown FIG. 3(a)), they do not significantly interact with muscles or cancel out the electrical current that needs to be deposited in the muscle region in order to provide suitable NMES therapy.

Preferable embodiments will use fixed positions of the stimulation electrodes and counter-signal producing electrodes. As such, empirical information may be used to determine a priori the most suitable counter signal for the control unit to deliver in order to most effectively cancel the NMES interference signal in remote regions. In various embodiments, this counter signal may be static, may be adjusted as needed based upon adjustments (ex. intensity, pulse width) to the signal being delivered to the stimulation electrodes for NMES, and/or may be calculated based on local factors such as control unit-measured impedance between either or both sets of electrodes. In some embodiments, the counter signal may be adjusted or fine-tuned manually by an operator, for example by an operator who is observing an ECG monitor and may adjust the counter signal such that use of the NMES device produces the least amount of interference.

In variations of the preferable embodiments, sensor systems may be used to measure the interference signal as it travels away from the region being treated with NMES. In these embodiments, one or more sensors can be utilized to help the control unit produce the most effective counter signal possible. Sensors may be utilized in a number of ways. In some embodiments, the sensors may be positioned to measure the interference signal (as in FIG. 4(a)), which can then be inverted and possibly scaled to produce a counter signal. In variation implementations, a sensor could be placed in a region distal to the electrodes used to deliver the counter signal (for example, as shown in FIG. 4(c)), and thus be positioned to measure any residual signal. Some implementations may use multiple sensors in one or both of these positions, or in other positions that will be clear to those skilled in the art. Depending on the embodiment, sensors may be built into a pad with the electrodes (fixing their relative positions), or may be placed discretely on the subject without the use of a pad. In some embodiments, multiple pads may be utilized to optimize the position of sensors and electrodes. Depending on the body part receiving NMES and the relative position of the monitoring equipment and/or device sensors where interference is intended to be minimized, sensors and counter signal electrodes may be placed in close proximity to the stimulation region (for example, as in FIG. 4(b)) or more remotely from the stimulation region (as in FIG. 4(e)).

Figure 5B:
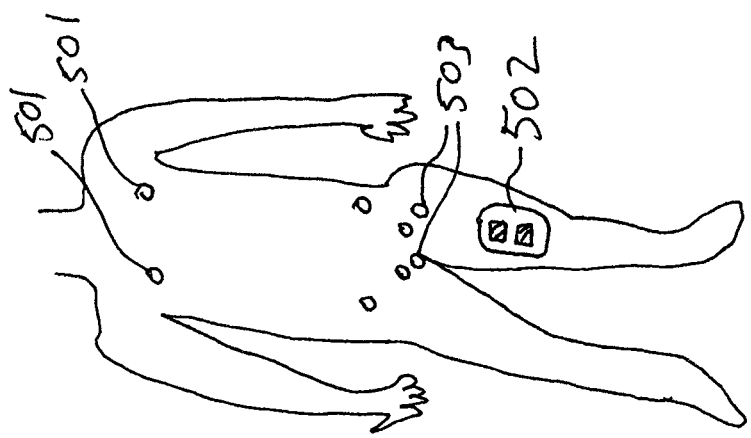
As shown in FIG. 5, variation embodiments of the devices and systems shown in multiple configurations.
Figure 5A:
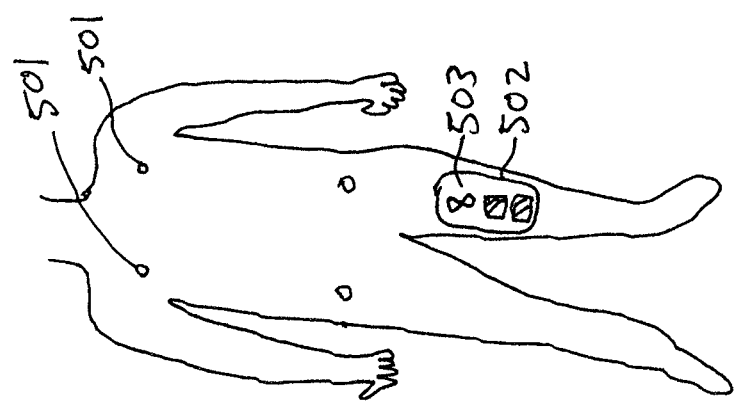

In some embodiments it may be desirable to minimize interference with more than one electrical sensor remote from the NMES site. For example, when using NMES in the presence of ECG monitoring, which requires multiple electrodes. In this situation, some embodiments may use simple configurations of counter signal producing electrodes (ex. FIG. 5(a)), while other embodiments will implement more advanced active cancellation techniques that account for different path lengths and directionality of the interference signal as it spreads away from the region of NMES. An example configuration of a more advanced active cancellation system (control unit not shown) is shown in FIG. 5(b).

Figure 6:
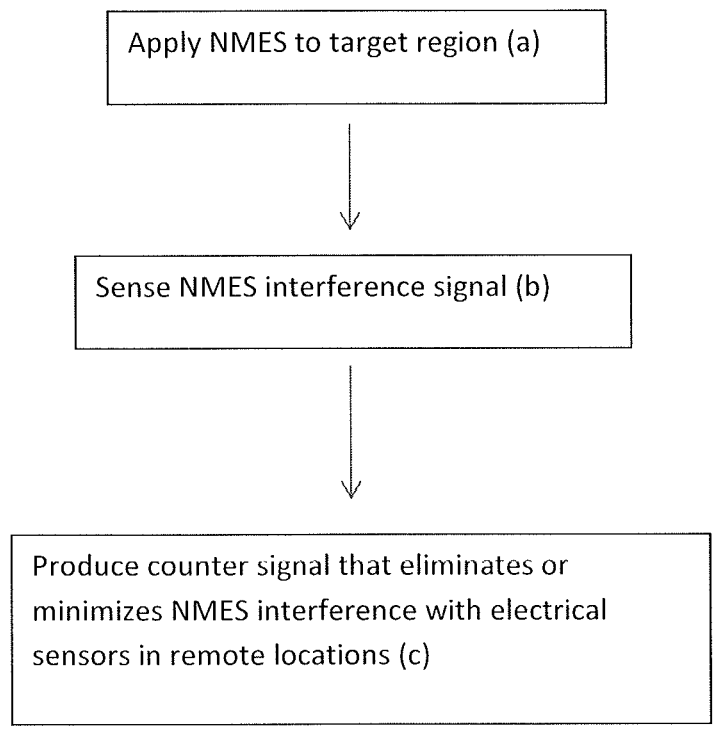
As shown in FIG. 6, several steps in one preferable embodiment of the method described herein.

In a preferable embodiment of the method described herein, one step would involve placing at least one stimulation electrode and at least one counter-signal producing electrode on the body of a subject. A later step would be applying stimulation energy to a body region of a subject, with sufficient enough amplitude to produce a muscle contraction. A simultaneous (or slightly later, depending on the configuration) step in the method is to apply a second active signal to the body, in the form of a counter signal, said counter signal having an appropriate shape, polarity, amplitude, and anatomical origin to effectively minimize or eliminate the interference the first stimulation energy signal produces in electrical measurements captured by sensors remote to the NMES region. In some embodiments of the method, an additional step involves using a sensor to estimate either the interference signal, the residual signal resulting after the counter signal is applied, or both, and adjusting the counter and/or NMES signal properties accordingly in order to minimize electrical interference with remote monitoring equipment and/or devices that require electrical sensing to function properly. An example embodiment of the method is shown in FIG. 6.

DESCRIPTION OF THE DRAWINGS

While preferable embodiments of the invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

As shown in FIG. 1, example preferable embodiments of the presently-disclosed devices and systems. In 1(a), control unit 101 contains an LCD touchscreen display/user interface as well as a number of controls, knobs, buttons, and dials. An interconnect cable 102 connects the control unit to pads 103 that contain both stimulation and counter signal electrodes. In 1(b), the subject-contacting side of pad 103 is shown, with an example configuration of stimulation 104 and counter signal producing 105 electrodes.

As shown in FIG. 2, variations of preferable embodiments of the devices and systems that include electrodes used to deliver NMES and electrodes used to produce a counter signal. In 2(a), a subject 201 is being monitored with four ECG electrodes 204 on his torso. A control unit 202 is connected to a pad 203 configured to provide NMES and counter signals to the leg. In (b), the pad 203 is configured so that counter signal electrodes 205 are located between stimulation electrodes 2044 and ECG monitoring sensor electrodes 204 (not shown in the FIG. 2(b)) when pad 203 is placed on the subject as shown in FIG. 2(a). In (c), shown is a different shaped pad 206 configured for another body part of the subject. In the embodiment shown, a different relative position of the counter signal electrodes 205 and stimulation electrodes 2044 is implemented. In (d), an embodiment that does not use a pad and instead uses discrete individual electrodes that can be placed on the subject in positions that the NMES operator deems appropriate is shown.

As shown in FIG. 3 various electrical signals associated with the devices, systems, and methods described herein. In all sub-figures, the y-axis represents relative voltage (not to scale) and the x-axis represents time (not to scale). All signals shown are approximate and for the purpose of example only. Please refer to (e) for clarification as the signals in sub-figures (a)-(d) are described. In (a), an example signal that a control unit 301 may provide to stimulation electrodes 302. In (b), an example signal that could be measured outside of the region of stimulation at location (1). In (c), a relatively smaller amplitude signal that could be measured further outside the region of stimulation at location (2). The signals shown in (b) and (c) are the interference signal that is produced as a byproduct of NMES signal (a) being applied in the intended region of stimulation. In (d), an example counter signal with similar amplitude but opposite polarity of the interference signal shown in (c), which can be applied at counter signal electrodes 303 to cancel out the interference signal and thus minimize the impact it could have on monitoring sensors and/or devices located more remotely to the region of NMES. In (e), an example system configuration, as well as annotated regions (1) and (2) that correspond to the signals shown in (b) and (c), respectively.

As shown in FIG. 4, variations of preferable embodiments of the devices and systems that include electrodes used to deliver NMES and electrodes used to produce a counter signal as well as sensors used in conjunction with the system. In (a), a system pad 401 contains a sensor 403 that is located between stimulation electrodes 402 and counter signal electrodes 404. In (b), a variation embodiment that uses multiple sensors 403. In (c), a further variation embodiment where the sensor 403 is positioned relatively further away from the zone of stimulation compared to the location of the counter signal electrodes 404. In (d), an embodiment that uses two system pads, a primary pad 401 that contains stimulation electrodes 402 and a secondary pad 405 that contains both a sensor 403 and a monopolar counter signal electrode 404. In (e), an embodiment of the systems and devices configured for use on the arm of a subject. Both the sensors 403 and the counter signal electrodes 404 are located in a position remote from the zone of stimulation.

As shown in FIG. 5, variation embodiments of the devices and system shown in multiple configurations. In (a), a system pad 502 is placed on a subject's leg, with counter signal producing sensors 503 located on the system pad in a region proximal to the zone of NMES but remote from the ECG sensors 501. A variation embodiment is shown in (b), where pad 502 contains only stimulation electrodes, and counter signal producing electrodes 503 are positioned relatively more remotely from the NMES site, closer to the monitoring sensors where it is desired to minimize any interference signal originating from the stimulation zone. In (b), several sets of counter signal producing electrodes are used to account for various directionality aspects of the interference signal as it travels to different ECG sensors 501.

As shown in FIG. 6, steps in one preferable embodiment of the method described herein. Shown are several example steps in a preferable embodiment of the method disclosed. Variations of this preferable method may skip the sensing step (b), relying on operator-set, internally-calculated, or pre-determined settings for the counter signal.

The invention claimed is:

1. A method of reducing interference in a muscle stimulation system, comprising:
    delivering an electrical muscle stimulation signal to a patient to stimulate muscle contraction;
    sensing an interference signal resulting from delivering the electrical muscle stimulation signal; and
    delivering an electrical counter signal to the patient that destructively interferes with the interference signal.

2. The method of claim 1 wherein delivering the electrical counter signal does not degrade the stimulating effect of the delivered electrical muscle stimulation signal.

3. The method of claim 1 wherein delivering the electrical counter signal minimizes or eliminates the interference signal.

4. The method of claim 1 wherein delivering the electrical counter signal comprises delivering an electrical counter signal that has an opposite polarity and substantially the same amplitude as the interference signal.

5. The method of claim 4 wherein delivering the electrical counter signal comprises delivering an electrical counter signal that has an amplitude less than an amplitude of the delivered electrical stimulation signal.

6. The method of claim 1 wherein delivering the electrical counter signal comprises delivering an electrical counter signal that has a shape that is different than a shape of the electrical muscle stimulation signal.

7. The method of claim 1 wherein the method further comprises modifying a parameter of the delivered electrical counter signal and delivering a second electrical counter signal with the modified parameter.

8. The method of claim 7 wherein modifying a parameter of the delivered electrical counter signal comprises modifying at least one of an amplitude, a phase, and a shape of the delivered electrical counter signal.

9. The method of claim 7 wherein modifying a parameter of the delivered electrical counter signal is in response to sensing the interference signal with an interference signal sensor.

10. The method of claim 1 further comprising sensing the interference signal with an interference signal sensor.

11. The method of claim 10 wherein sensing the interference signal with an interference signal sensor comprises sensing the interference signal at a location different than where the muscle stimulation signal is delivered to the patient and where the counter signal is delivered to the patient.

12. The method of claim 10 wherein sensing the interference signal with an interference signal sensor comprises sensing the interference signal at a location between where the muscle stimulation signal is delivered to the patient and where the counter signal is delivered to the patient.

13. The method of claim 1 wherein delivering an electrical counter signal is in response to sensing the interference signal.

14. The method of claim 1 further comprising sensing a physiological signal from the patient, and wherein delivering the counter signal reduces interference between the sensed physiological signal and the interference signal.

15. The method of claim 14 wherein sensing a physiological signal from the patient comprises sensing an EKG signal from the patient, and delivering the counter signal reduces interference between the EKG signal and the interference signal.

* * * * *